(12) United States Patent
Choi

(10) Patent No.: US 9,987,106 B2
(45) Date of Patent: Jun. 5, 2018

(54) ORTHODONTIC SELF-LIGATING BRACKET

(71) Applicant: Jeng Soo Choi, Hwaseong-si (KR)

(72) Inventor: Jeng Soo Choi, Hwaseong-si (KR)

(*) Notice: Subject to any disclaimer, the term of this patent is extended or adjusted under 35 U.S.C. 154(b) by 0 days. days.

(21) Appl. No.: 15/023,857

(22) PCT Filed: Apr. 18, 2014

(86) PCT No.: PCT/KR2014/003400
§ 371 (c)(1),
(2) Date: Mar. 22, 2016

(87) PCT Pub. No.: WO2015/111799
PCT Pub. Date: Jul. 30, 2015

(65) Prior Publication Data
US 2016/0228217 A1    Aug. 11, 2016

(30) Foreign Application Priority Data
Jan. 27, 2014  (KR) .................. 10-2014-0009507

(51) Int. Cl.
  *A61C 3/00*    (2006.01)
  *A61C 7/28*    (2006.01)
  *A61C 7/14*    (2006.01)
  *A61C 7/30*    (2006.01)
(52) U.S. Cl.
  CPC .............. *A61C 7/287* (2013.01); *A61C 7/14* (2013.01); *A61C 7/30* (2013.01)
(58) Field of Classification Search
  CPC .............. A61C 7/14; A61C 7/30; A61C 7/287
  USPC ...................................... 433/8–17
  See application file for complete search history.

(56) References Cited

U.S. PATENT DOCUMENTS

| | | | | |
|---|---|---|---|---|
| 6,247,923 B1* | 6/2001 | Vashi | ...................... | A61C 7/287 433/10 |
| 6,257,883 B1* | 7/2001 | Voudouris | ................ | A61C 7/02 433/11 |
| 8,550,814 B1* | 10/2013 | Collins | ..................... | A61C 7/12 433/17 |
| 2004/0072117 A1* | 4/2004 | Farzin-Nia | ............... | A61C 7/20 433/10 |
| 2009/0305183 A1* | 12/2009 | Chen | ........................ | A61C 7/14 433/8 |

(Continued)

FOREIGN PATENT DOCUMENTS

| | | |
|---|---|---|
| JP | 2009-207930 A | 9/2009 |
| JP | 2012-500053 A | 1/2012 |

(Continued)

*Primary Examiner* — Yogesh Patel
*Assistant Examiner* — Gwen M Demosky
(74) *Attorney, Agent, or Firm* — Novick, Kim & Lee, PLLC; Jae Youn Kim

(57) ABSTRACT

Provided is an orthodontic self-ligating bracket in which the second wing formed on the bracket body is formed to be lower than the height of the first wing, and when pushing the wire to the slot to mount the wire to the slot by installing the wire coupling device on the top surface of the second wing, while the plate tip is pushed rearward by the force for pushing the wire, the slop inlet is open, and when the wire is mounted on the slot and the pushing force disappears, the plate tip closes the slot inlet, thereby remarkably shortening the wire mounting time and allowing very convenient wire mounting.

7 Claims, 5 Drawing Sheets

(56) References Cited

U.S. PATENT DOCUMENTS

| | | | |
|---|---|---|---|
| 2009/0325120 A1* | 12/2009 | Lewis | A61C 7/287 433/13 |
| 2010/0203463 A1 | 8/2010 | Huff et al. | |
| 2011/0269093 A1* | 11/2011 | Waugh, Jr. | A61C 7/287 433/10 |
| 2013/0157214 A1* | 6/2013 | Chen | A61C 7/303 433/11 |

FOREIGN PATENT DOCUMENTS

| | | |
|---|---|---|
| JP | 2012-510835 A | 5/2012 |
| KR | 10-0660646 B1 | 12/2006 |
| KR | 10-0763315 B1 | 10/2007 |
| KR | 10-1016416 B1 | 2/2011 |

* cited by examiner

ORTHODONTIC SELF-LIGATING BRACKET

CROSS-REFERENCE TO RELATED APPLICATIONS

This application is a national-stage entry under 35 USC 371 of International Application No. PCT/KR2014/003400 filed on Apr. 18, 2014, and claims benefit of priority of Korean Patent Application No. 10-2014-0009507, filed on Jan. 27, 2014, in the Korean Intellectual Property Office, which is hereby incorporated by reference in its entirety.

BACKGROUND OF THE INVENTION

Field of the Invention

The present invention relates to a orthodontic self-ligating bracket in which a second wing formed on the bracket body is formed to be lower than a height of a first wing, a wire coupling device is installed on the upper surface of the second wing, when pushing the wire into a slot to mount the wire in the slot, an inlet of the slot is open, while a plate tip is pushed rearward by the force for pushing the wire, and when the wire is mounted in the slot and the pushing force disappears, the plate tip closes the slot inlet, thereby significantly shortening the wire mounting time and allowing very convenient wire mounting.

Description of the Related Art

In general, orthodontics is to correct irregular dentition and should be targeted to abnormality of the tissues around the teeth that impair the dentition. The orthodontics also includes orthodontic of a so-called malocclusion such as abnormality of occlusion and prognathism of a lower jaw and an upper jaw, in addition to the abnormality of dentition. An orthodontic device is preferably cured at around 8 to 9 years of age to 13 to 15 years of age when primary teeth are replaced with permanent teeth, and a duration of the treatment takes from six months one or two years. In addition, the orthodontic is constituted by a plurality of brackets fixed by being attached to each of the teeth on one side and a wire connecting the plurality of brackets, and correctly corrects the teeth by the pulling force for the wire.

As an example of such a orthodontic bracket, Korean Patent Registration No. 0862631 discloses a technique of "an orthodontic bracket formed with a slot on one side and an attachment surface attached to the surfaces of the teeth on the other side, in which polymer powders are soldered to the attachment surface of the bracket so that a part of a lower end is melted and stuck, and the bracket is formed so that an adhesive permeates a lower end gap of the polymer powders, 20% to 30% of the size of the particles of the polymer powders fused to the attachment surface of the bracket are fused to the attachment surface by being melt, and a wetting angle of the particles is 50° to 70°, and a method for manufacturing a bracket used in the orthodontic bracket, the method including: a machining step of forming a bracket formed with a slot on one side and an attachment surface on the other side; a transparency dilution step for diluting transparency by performing polishing so that light reflectivity of the bracket formed through the machining step; and a polymer power fusing step of fusing the polymer powers to the attachment surface of the bracket formed through the machining step and forming the polymer powders so that the adhesive permeates into the gap of the polymer powders to maximize the adhesion efficiency".

Further, the Korean Patent Registration No. 1016416 discloses a "teeth fixing bracket for attaching a wire for applying a force to the teeth to the teeth to move the teeth to a desired position, the bracket including: a bracket body section to which a wire is fixed; and a detachable attachment means that is coupled to the bracket body section and is removably attached to the teeth surfaces".

Further, Korean Patent Registration No. 660646 discloses a technique of a "orthodontic bracket that includes a body section having an external form for being attached to teeth; a coating layer formed on the opposite surface of the slot; and a slot formed between the body section and the coating layer so that a coating layer is drawn inward to increase a coating amount".

Further, Korean Patent Registration No. 0763315 discloses a technique of an "orthodontic bracket using an arch wire, the bracket including: a bracket base fixed to the surfaces of the teeth; and a wire holder removably mounted to the bracket base and immovably fixed to the arch wire, wherein the arch wire is immovably fixed to a holder, after being operated to apply force for movement of the teeth to a predetermined target position of the teeth".

However, since the conventional bracket needs to be bound so that the wire does not leave from the slot, after fitting and mounting the wire to the slot, there were technical problems in which much work is required, cumbersome work is needed and a time for wire mounting is long.

SUMMARY OF THE INVENTION

An aspect of the present invention is directed to provide an orthodontic self-ligating bracket in which a second wing formed on a bracket body is formed to be lower than a height of a first wing, a wire coupling device is installed on the upper surface of the second wing, when pushing the wire into a slot to mount the wire in the slot, an inlet of the slot is open, while a plate tip is pushed rearward by the force for pushing the wire, and when the wire is mounted in the slot and the pushing force disappears, the plate tip closes the slot inlet, thereby significantly shortening the wire mounting time and allowing very convenient wire mounting.

To achieve the above object, according to the present invention, there is provided an orthodontic self-ligating bracket that is configured to include a bracket body that has a slot formed at a center of an opposite side of a base side releasably affixed to a tooth at a location to which a wire is mounted during orthodontic treatment, a first wing formed to protrude upward at the front around the slot, and a second wing formed to protrude upward at the rear around the slot to correspond to the first wing and formed to be lower than the height of the first wing; and a coupling device that is coupled to an upper surface of the second wing at a bottom surface having a size corresponding to the upper surface of the second wing, and in which when pushing the wire into the slot to mount the wire to the slot, while the tip blocks the inlet of the slot, the slot inlet is open while the tip is pushed rearward, the wire is mounted on the slot, and the tip closes the inlet of the slot.

Further, the bracket body is formed with a wing dividing groove that is formed to be orthogonal to the slot at the center of the side on which the slot is formed so that the first wing and the second wing form a pair by bisecting the first wing and the second wing.

Further, the wire coupling device is configured to include an adaptor in which a bottom surface part is formed to have a size corresponding to the upper surface of the second wing forming a pair, and an upper surface coincides with the upper surface of the first wing when seating and coupling to the upper surface of the second wing; and a plate that is slidably coupled to the top of the adaptor, and in which when pushing the wire to the slot to mount the wire to the slot, while the tip blocks the inlet of the slot, the slot inlet is open, while the tip of the slot is pushed rearward by the force for pushing the wire, and when the wire is mounted on the slot, the force for pushing the tip disappears, the tip blocks the inlet of the slot, while touching the side surface of the first wing Further, the adaptor is configured to include an operating space that is formed to pass through the upper inside and is formed in a slope form in which a width becomes wider as it goes from the top to the bottom; a housing groove that is formed at the center of a sliding surface below the operating space so that a semicircular part of a micro-spring, and is formed in a semicircular shape corresponding to a semicircle of the micro-spring; a semicircular foreign matter preventing bump that is installed at an outer end of the sliding surface to prevent foreign matters from entering the interior of the housing groove; an operating groove that is formed at an inner end of the housing groove and communicates with the housing groove on the inner side surface; and a coupling protrusion that is formed to protrude downward at the bottom surface center so that the bottom surface part comes into close contact with and is coupled to the top surface of the second wing forming a pair Furthermore, the plate is configured to include a body that is fitted to the operating space and slides along the operating space, while being formed to have an external form corresponding to the operating space of the adaptor, and in which a tip is located in the inlet of the slot to open and close the slot inlet; a semicircular groove that is formed at the center of the body bottom surface, and in which an outside end is fitted to the semicircular foreign matter preventing bump, while wrapping the upper semicircle of the micro-spring exposed from the housing groove to correspond to the housing groove when coupling the plate to the operating space; and a hooking bump that is formed on the tip bottom surface and is fitted to the operating groove, while sliding along the operating groove, when pushing the wire into the slot inlet to mount the wire to the slot, the micro-spring is pushed rearward and is contracted, and while the wire is mounted to the slot and is pushed forward by the restoration force of the contracted micro-spring, the tip blocks the slot inlet.

Further, a material diameter of the micro-spring may be equal to or less than 0.1 mm.

In addition, the micro-springs may have a coil outer diameter of 0.6 mm, a length of 1 mm and the number of coils of 3 or 4.

In addition, the orthodontic self-ligating bracket may be made of a transparent body and may be a non-metallic material.

In addition, the slope of the operating space, and both slopes of the plate corresponding thereto may be designed by 45°.

According to the present invention, since the second wing formed on the bracket body is formed to be lower than the height of the first wing, and when pushing the wire to the slot to mount the wire to the slot by installing the wire coupling device on the top surface of the second wing, while the plate tip is pushed rearward by the force for pushing the wire, the slot inlet is open, and when the wire is mounted on the slot and the pushing force disappears, the plate tip closes the slot inlet, and thus, there is an effect in which the wire mounting time is remarkably shorted and the wire mounting is very convenient.

BRIEF DESCRIPTION OF THE DRAWINGS

The above and other aspects, features and advantages of certain exemplary embodiments of the present invention will be more apparent from the following description taken in conjunction with the accompanying drawings, in which.

DETAILED DESCRIPTION OF EXEMPLARY EMBODIMENTS

Figure 1:
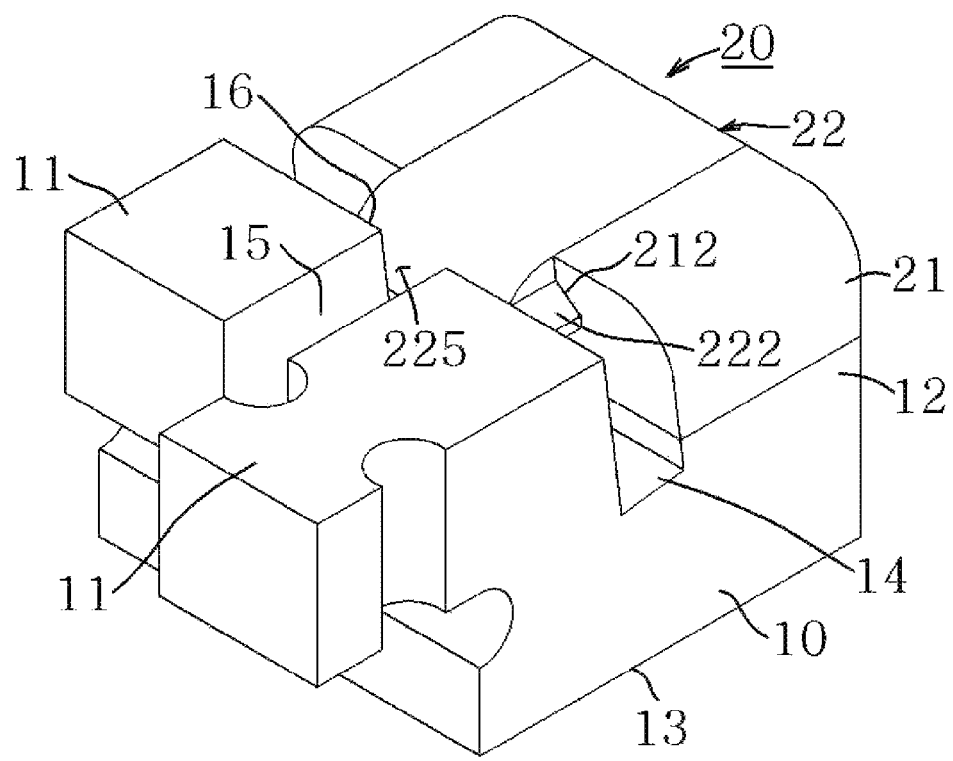
FIG. 1 is a perspective view according to an embodiment of the present invention.

Exemplary embodiments of the present invention will be described below in detail with reference to the accompanying drawings. Wherever possible, the same reference numerals will be used to refer to the same elements throughout the specification, and a duplicated description thereof will be omitted. It will be understood that although the terms "first", "second", etc. are used herein to describe various elements, these elements should not be limited by these terms. These terms are only used to distinguish one element from another element.

Hereinafter, a configuration of an orthodontic self-ligating bracket according to the present invention will be described with reference to the accompanying drawings.

Figure 2:
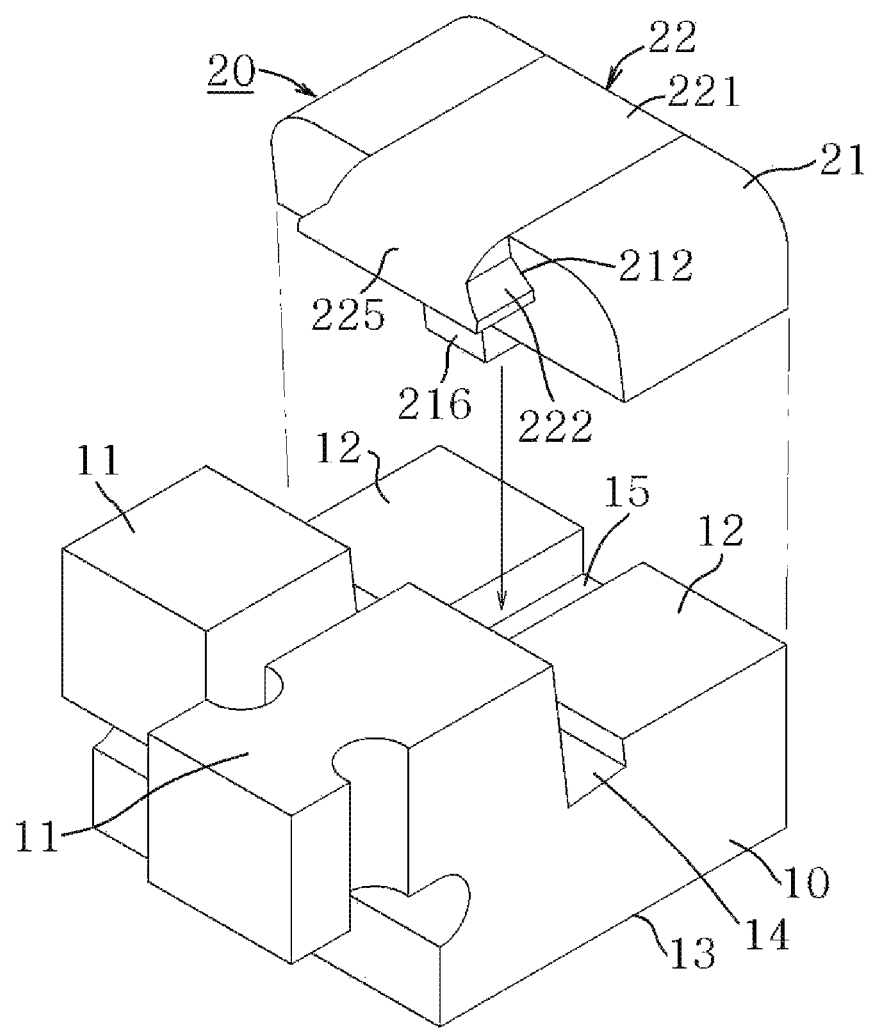
FIG. 2 is an exploded perspective view of the embodiment of the present invention.
Figure 3:
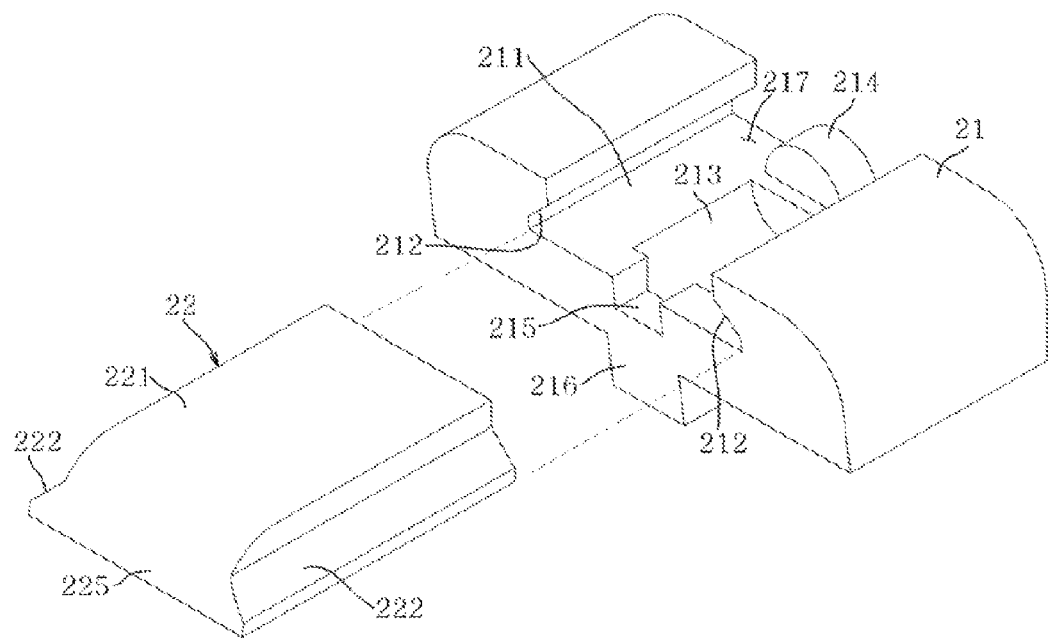
FIGS. 3 and 4 are exploded perspective view of an adapter and a plate according to an embodiment of the present invention.

As illustrated in FIGS. 1 to 3, the self-ligating bracket orthodontic according to the present invention is configured to include a bracket body 10 which includes a base surface 13 releasably affixed to a tooth during orthodontic treatment, a slot 14 formed on a back surface of the base surface 13, and a first wing 11 and a second wing 12 formed before and after the slot 14; and a wire coupling device 20 attached to the upper surface of the second wing 12 of the bracket body 10.

Specifically, the bracket body 10 is configured to include a base surface 13 serving as a surface releasably affixed to a tooth during orthodontic treatment, a slot 14 which is formed along the center of the other surface of the base surface 13 and to which the wire 40 is mounted, a first wing 11 formed to protrude upward at the front around the slot 14, a second wing 12 formed to be lower than the height of the first wing 11, while being formed to protrude upward at the rear around the slot 14, and a wing slip groove 15 that is formed to be orthogonal to the slot 14 at the center of the surface on which the slot 14 is formed so that the first wing 11 and the second wing 12 are bisected and each pair of first wings 11 and second wings 12 is provided.

The second wing 12 is cut by the height of the wire coupling device 20 after being manufactured at the same height as the first wing 11 at the time of manufacture, and is formed to be lower than the height of the first wing 11.

The wire coupling device 20 is configured to include an adaptor 21 that is formed at the same height of the cut height of the second wing 12 and is closely coupled to the top surface of the second wing 12 at the bottom surface, and a plate 22 coupled to the upper operating space 211 of the adaptor 21

Specifically, a coupling protrusion 216 is formed to be closely coupled to the wing dividing groove 15 and protrudes downward at the center of the bottom surface. Since the coupling protrusion 216 is fitted correspondingly to the wing dividing groove 15 between the pair of second wings 12 when coupling the adaptor 21 to the top surface of the second wing 12, it can be easily coupled without the need for aligning the center. When coupling the adaptor 12 to the top surface of the second wing 12, it is desirable to couple by applying the adhesive on the bottom surface of the adapter 21.

Figure 4:
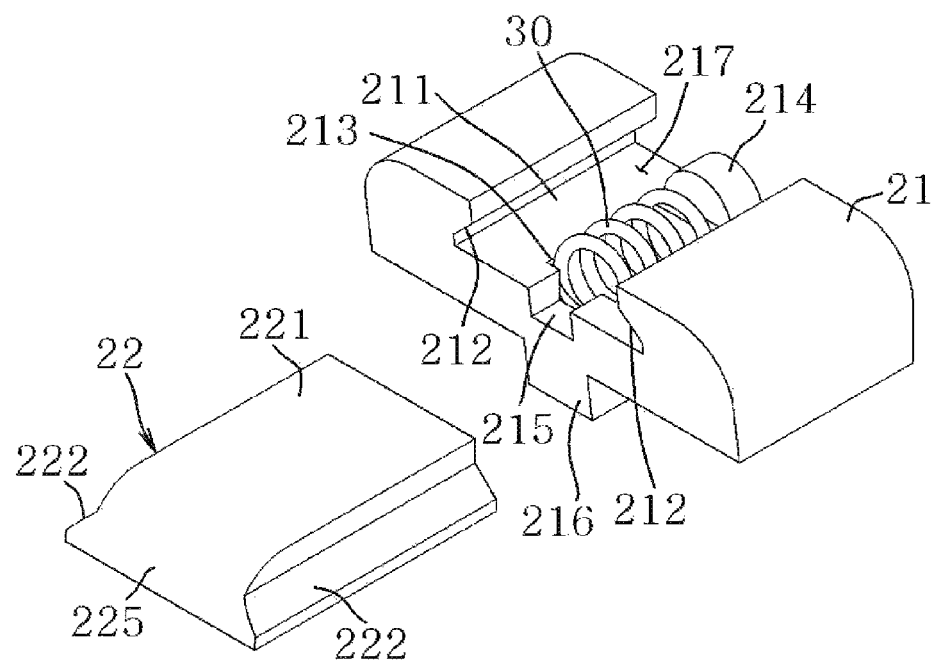

The operating space 211 is formed through the upper portion of the adapter 21, as illustrated in FIGS. 3 and 4. The operating space 211 is formed in the form of a slope 212 of narrow top and wide bottom in which the widths of both left and right become wider in the open state of the upper portion. At this time, the slope 212 of the left and right sides is preferably to be formed to form 45° with the sliding surface 217 so that it is dynamically stable, the distribution rate of force is great, and the overall supporting force increases.

A housing groove 213 to which the micro-spring 30 is inserted and coupled is formed at the center of the sliding surface 217 below the operating space 211 of the adaptor 21. The housing groove 213 is formed in a semicircular form corresponding to the semicircle of the micro-spring 30. When the circular micro-spring 30 is inserted to the housing groove 213, as illustrated in FIG. 4, the lower semicircle enters the housing groove 231 and the upper circle is in an exposed state.

A semicircular foreign matter preventing bump 214 for preventing foreign matters from entering the interior of the housing groove 213 is formed at the outer end of the sliding surface 217.

Further, at the inner end of the housing groove 213, an operating groove 215 is formed to communicate with the housing grove 213 on the inner surface. On the operating groove 215, a hooking bump 224 is coupled which pushes and contracts the micro-spring 30 coupled to the housing groove 213 of the plate 22.

The plate is coupled to the operating space 211 of the adaptor 21 and slidably moves along the operating space 211, and the tip 225 serves to open and close the inlet 16 of the slot. An external form of the plate 22 corresponds to the operating space 211. Both left and right slopes 222 of the plate 22 are formed at 45° likewise the slope 212 of the operating space 211.

Figure 5:
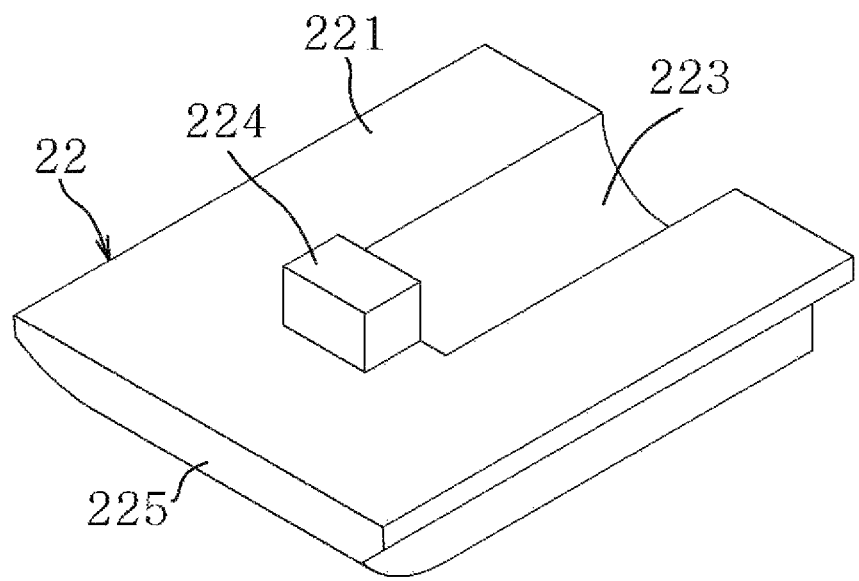
FIG. 5 is a bottom perspective view of a plate according to an embodiment of the present invention.
Figure 6:
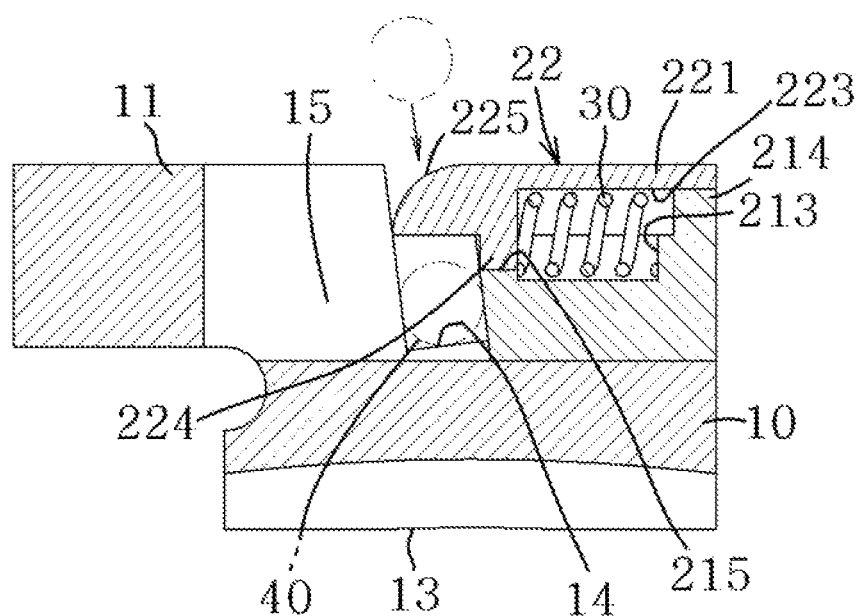
FIG. 6 is a side cross-sectional view of the present invention according to a first embodiment.

At the bottom center of the tip 255 of the body 221 of the plate 22, as illustrated in FIGS. 5 and 6, a hooking bump 224 coupled to the operating groove 215 of the adaptor 21. Moreover, a semicircular groove 223 is formed at the bottom center of the plate 22. The semicircular groove 223 provides a space in which the extension and contraction operations of the micro-spring 30 can be performed while the micro-spring 30 is not exposed to the outside, by wrapping the upper semicircle of the micro-spring 30 exposed from the housing groove 231 corresponding to the housing groove 213 when coupling the plate 22 to the operating space 211 of the adaptor 21. Further, when coupling the plate 22 to the operating space 211, the outer end of the semicircular groove 223 coincides with the semicircular foreign matter preventing bump 214.

Figure 7:
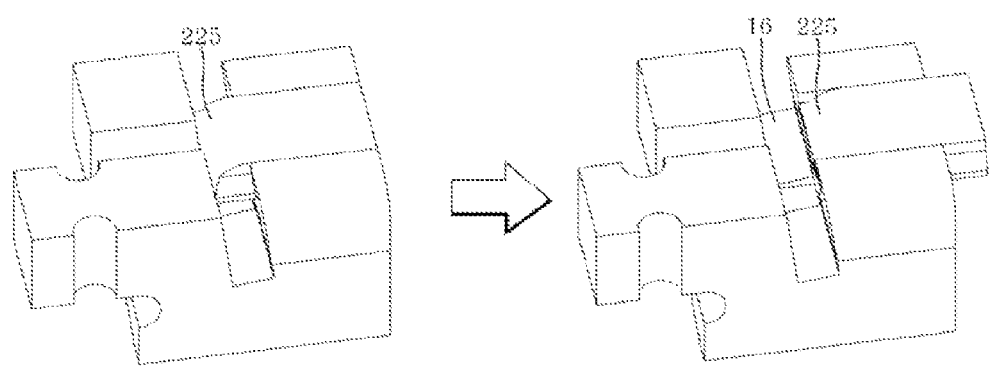
FIG. 7 is a diagram illustrating an operating state according to an embodiment of the present invention.

In the plate 22 coupled to the operating space 211 of the adaptor 21, when pushing the wire into the slot 14 to mount the wire 40 to the slot 14 in the state in which the tip 225 initially touches the side surface of the first wing 11 to block the slot inlet 16 as illustrated in FIG. 7, the tip 225 of the plate 22 is pushed rearward by the force for pushing the wire 40. At this time, since the hooking bump 224 pushes the micro-spring 30 in the housing groove 213, the micro-spring 30 is contracted.

When the wire 40 is mounted on the slot 14, the force pushing the plate tip disappears, while the contracted spring 30 is restored to an original state, it pushes the hooking bump 224 toward the first wing 11. Thus, the tip 225 of the plate 22 blocks the slot inlet 16, and the wire 40 mounted in the slot 14 is in a state in which the wire cannot leave the slot 14.

The micro-spring 30 preferably has a material diameter of 0.1 mm or less, a coil outer diameter of 0.6 mm, a length 1 mm and the number of coils of 3 or 4, and the orthodontic self-ligating bracket according to the present invention is preferably made of non-metallic material of the transparent body so that it does not appear at the time of adhering to the teeth for orthodontic.

Thus, since the present invention is a transparent body of non-metallic material, it is inconspicuous even when adhering to the teeth during orthodontic, and it can give a satisfaction feeling. In the configuration of the present invention, although the micro-spring 30 is a metal, as described above, since the material diameter is minute and is inconspicuous even when being coupled with the transparent non-metallic material, the present invention is a product with excellent aesthetic properties, such as there is no feeling of rejection after adhering to the teeth.

As described, according to the present invention, the second wing 12 formed on the bracket body 10 is formed to be lower than the height of the first wing 11, and when pushing the wire 40 to the slot 14 to mount the wire 40 to the slot 14 by installing the wire coupling device 20 on the top surface of the second wing 12, while the plate tip 225 is pushed rearward by the force for pushing the wire 40, the slot inlet 16 is open, and when the wire 40 is mounted on the slot 14 and the pushing force disappears, the plate tip closes the slot inlet 16, thereby remarkably shortening the wire mounting and facilitating the wire mounting.

The base surface 13 of the bracket body 10 is releasably affixed to a tooth for orthodontic treatment. When the attachment of the bracket body 10 to the teeth to be corrected is completed, as illustrated in FIG. 6, the wire 40 is mounted on the slot 14.

Initially, the tip 225 of the plate 22 is in the state of blocking the slot inlet, when pushing the wire 40 into the slot 14 to mount the wire 40 to the slot 14, while the plate tip 225 is pushed rearward by the force for pushing the wire 40 as illustrated in FIG. 7, the slot inlet 16 is open, and the wire 40 enters a state in which it can be mounted to the slot 14. At this time, the plate tip 225 is pushed rearward, and at the same time, the holing bump 224 pushes the micro-spring 30 and the micro-spring 30 becomes a contracted state.

When the wire 40 is mounted on the slot 14, the force pushing the late tip 225 disappears, the length of the contracted micro-spring 30 is restored to an original state and pushes the hooking bump 224 to the first wing 11 side. As the hooking bump 224 is pushed, the plate tip 225 is brought into close-contact with the side surface of the first wing 11 to block the slot inlet 16, and the wire 40 mounted on the slot 14 enters a state in which it cannot leave the slot 14.

In this way, according to the present invention, since the wire 40 can be mounted on the slot 14 only by pushing the slot 14, it is possible to remarkably shorten the mounting time of the wire 40 and the mounting of the wire 40 is very convenient While the invention has been illustrated and described with reference to exemplary embodiments thereof, it will be understood by those skilled in the art that various changes in form and details may be made therein without departing from the spirit and scope of the invention as defined by the appended claims. Therefore, the scope of the invention is defined not by the detailed description of the invention but by the appended claims, and all differences within the scope will be construed as being included in the present invention.

What is claimed is:

1. An orthodontic self-ligating bracket comprising:
a bracket body including:
a slot formed at a center of an opposite side of a base side of the bracket body, the base side being configured to be attached to an anterior facing surface of a tooth at a location to which a wire is mounted during orthodontic treatment;
a first wing formed on a front side of the slot and protruding upward;
and
a second wing formed on a rear side of the slot and protruding upward with a height lower than that of the first wing; and
a wire coupling device including:
an adaptor having a bottom surface seated and coupled to an upper surface of the second wing; and
a plate slidably coupled to a top of the adaptor,
wherein the bracket body has a wing dividing groove disposed to be orthogonal to the slot, and
wherein the plate has a tip configured to close an inlet of the slot before a wire is mounted into the slot and configured to be pushed rearward to open the inlet of the slot by a press-contact of the wire thereby mounting the wire into the slot, and a micro-spring attached to the plate and configured to move the plate to close the inlet of the slot at the substantially same time as the mounting of the wire is completed, wherein the adaptor includes:
an operating space that is formed to pass through an upper inside and is formed in a slope form in which a width becomes wider as it goes from a top to a bottom;
a housing groove that is formed at a center of a sliding surface below the operating space and in a semicircular shape corresponding to a semicircular shape of the micro-spring;
a semicircular foreign matter preventing bump that is installed on an outer end of the sliding surface to prevent foreign matters from entering an interior of the housing groove;
an operating groove that is formed adjacent to an inner end of the housing groove and communicates with the housing groove; and
a coupling protrusion that is formed to protrude downward at a bottom surface center of the adaptor so that the bottom surface of the adaptor comes into close contact with and is coupled to the upper surface of the second wing.

2. The orthodontic self-ligating bracket of claim 1, wherein the plate includes:
a plate body that is fitted to the operating space and slides along the operating space;
a semicircular groove that is formed at a center of a bottom surface of the plate body, in which a rear end thereof is fitted to the semicircular foreign matter preventing bump, for wrapping an upper semicircular part of the micro-spring exposed from the housing groove to correspond to the housing groove, when coupling the plate to the operating space; and a hooking bump that is formed on the bottom surface of the tip and is fitted to the operating groove, while sliding along the operating groove, when pushing the wire into the slot inlet to mount the wire to the slot, the micro-spring is pushed rearward and is contracted, and after the wire is mounted to the slot, the tip is pushed forward by the restoration force of the contracted micro-spring and blocks the slot inlet.

3. The orthodontic self-ligating bracket of claim 2, wherein a diameter of the micro-spring is equal to or less than 0.1 mm.

4. The orthodontic self-ligating bracket of claim 2, wherein the slope of the operating space, and both slopes of the plate corresponding thereto are 45 degrees.

5. The orthodontic self-ligating bracket of claim 3, wherein the micro-springs has a coil outer diameter of 0.6 mm, a length of 1 mm and the number of coils is 3 or 4.

6. The orthodontic self-ligating bracket of claim 5, wherein the orthodontic self-ligating bracket is made of a transparent body and is a non-metallic material.

7. An orthodontic self-ligating bracket comprising:
a bracket body including:
a base side configured to be attached to a tooth;
a slot disposed on an opposite side to the base side;
a first wing disposed on a front side of the slot; and
a second wing disposed on a rear side of the slot, wherein a height of the second wing is lower than that of the first wing; and
a wing dividing groove disposed to be orthogonal to the slot; and
a wire coupling device including:
an adaptor having a bottom surface seated and coupled to an upper surface of the second wing; and
a plate slidably coupled to a top of the adaptor,
wherein the adaptor includes:
an operating space disposed on an upper side thereof for receiving the plate, wherein the plate is movable in the operating space;
a housing groove disposed below the operating space for receiving a spring;
an operating groove disposed adjacent to an inner end of the housing groove and communicating with the housing groove; and
a coupling protrusion disposed to protrude downward at a center of the bottom surface of the adaptor so that the bottom surface of the adapter comes into close contact with and is coupled to the upper surface of the second wing, and
wherein the plate includes:
a plate body fitted to the operating space and slides along the operating space;
a semicircular groove disposed on a bottom surface of the plate body and elongated from a rear end of the plate to a point having a distance from a front end of the plate for covering an upper side of the spring exposed from the housing groove; and
a hooking bump located at a front end of the semicircular groove, protruding downward and fitted to the operating groove, wherein the hooking bump is in contact with the spring and configured to contract the spring when a front end of the plate is pressed down by the wire.

* * * * *